(12) United States Patent
Ryu

(10) Patent No.: US 6,818,653 B1
(45) Date of Patent: Nov. 16, 2004

(54) 6,7-DISUBSTITUTED -5,8-QUINOLINEDIONE DERIVATIVES AS AN ANTIFUNGAL AGENT

(75) Inventor: Chung Kyu Ryu, Seoul (KR)

(73) Assignee: Il Jin Copper Foil Corp. (KR)

( * ) Notice: Subject to any disclaimer, the term of this patent is extended or adjusted under 35 U.S.C. 154(b) by 0 days.

(21) Appl. No.: 09/979,830
(22) PCT Filed: May 4, 2000
(86) PCT No.: PCT/KR00/00426
§ 371 (c)(1), (2), (4) Date: Jun. 18, 2002
(87) PCT Pub. No.: WO01/12605
PCT Pub. Date: Feb. 22, 2001

(51) Int. Cl.⁷ .................. A61K 31/47; C07D 215/38
(52) U.S. Cl. .................. 514/312; 514/313; 546/171; 546/153
(58) Field of Search .................. 546/171, 153; 514/312, 313

(56) References Cited

FOREIGN PATENT DOCUMENTS

DE 4208874 A1 9/1993
EP 519290 * 9/1992

OTHER PUBLICATIONS

Jalpana Roy et al. Caplius enlish Abstract 1981:30533 Caplus DN 94:30533 Reaction of 6–arylamino–7–bromoquinoline–5,8–dione with nucleophiles (1980), 19B(6), 512–13.*

Gopalachari et al. English Abstract Caplus 1962:456172 Caplus DN 57:56172 57:11160c–i,11161a–d Potential amebicides. XV. Synthesis of 7–(and 6,7–di)substituted quinoline–5,8–quinones and 7–substituted 5–pchlorobenzoyl–(and benzyl)–8–hydroxyquinoline.*

Ryu, Chang–Kyu et al The antifungal activities of some 6–[N–(halophenyl)amino]–7–chloro–5,8–quinolinediones against Candida species (1994), 17(6), 483–6. (English Abstract Caplus).*

Bowman et al., Antimetabolites of Coenzyme Q.14. Quinolinequinone Analogs Which Inhibit Mitochondrial DPN–H–Oxidase and Succinoxidase, *Journal of Medicinal Chemistry*, vol. 16, No. 3, 206–209, 1973.

Roberts et al., The Site of Inhibition of Mitochondrial Electron Transfer by Coenzyme Q Analogues, *Arch. Biochem. Biophys.*, vol. 191, No. 1, 306–315, 1978.

* cited by examiner

*Primary Examiner*—R Desai
(74) *Attorney, Agent, or Firm*—Jones Day

(57) ABSTRACT

Novel 6,7-disubstituted-5,8-quinolinedione derivatives of general formula (I) or the process for the preparation thereof, wherein $R_1$ is $C_1$–$C_{20}$ alkylmercapto or phenylamino substituted by up to 3 groups selected from halogen, aceto; $R_2$ is halogen, thiocyano or $C_1$–$C_{20}$ alkylmercapto, are useful as an antifungal agent.

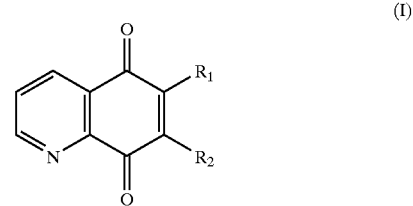

(I)

10 Claims, 2 Drawing Sheets

6,7-DISUBSTITUTED-5,8-QUINOLINEDIONE DERIVATIVES AS AN ANTIFUNGAL AGENT

BACKGROUND OF THE INVENTION

1. Field of the Invention

Figure 1:
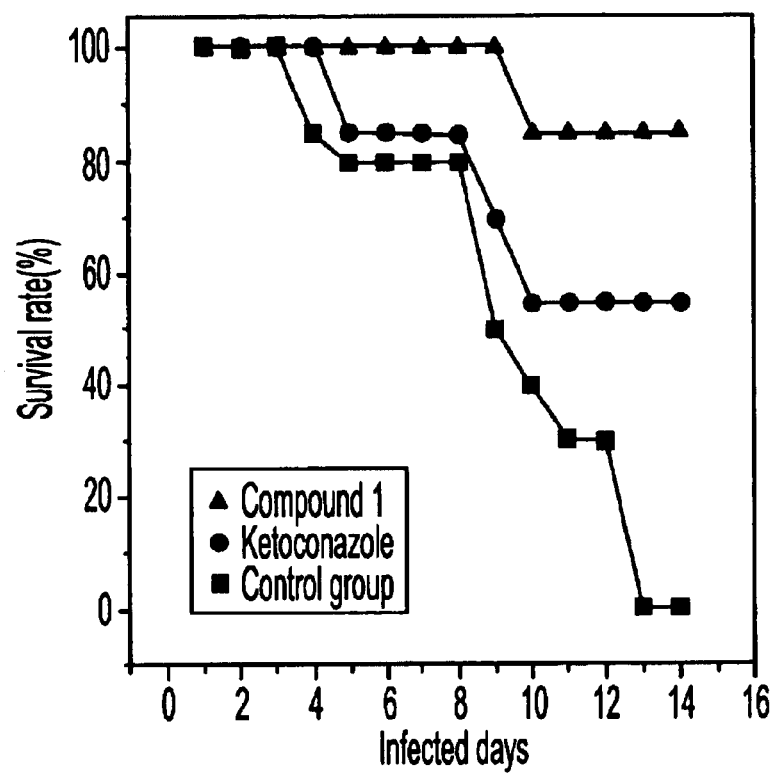

The present invention relates to 6,7-disubstituted-5,8-quinolindion derivatives as an antifungal agent expressed in the following formula 1 which has excellent antifungal activity against funges infecting human and animals,

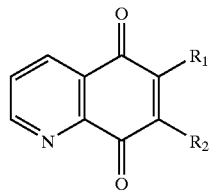
(I)

wherein $R_1$ represents phenylamino group substituted 1 to 3 with a substituent selected from the group consisting of a halogen atone and an aceto group, or $C_1$–$C_{20}$ alkylmercapto group; and $R_2$ represents thiocyano group; or $C_1$–$C_{20}$ alkylmercapto group.

2. Description of the Prior Art

The recent increase of fungal infections has generated a renewed interest in antifungal drugs, including development of new antifungal agents. We focused on developing 6,7-disubstituted-5,8-quinolinediones with noble mode of antifungal activities. As antimetabolites of coenzyme Q, the 6-(substituted)-7-chloro-5,8-quinolinediones inhibit mitochondrial Co-Q dependent succinoxidase and electron transport in *Saccaromyces cerevisiae*, that may be correlated with antifungal activity (*Arch. Biochem. Biophys.*, 191, 306–315, 1978). The 5,8-quinolindiones, as antimetabolites of coenzyme Q, inhibit cytochrome bc complex due to blockade of mitochondrial electron transport in fungi (*J. Med. Chem.*, 16, 206–209, 1973). 6/7-Substituted-5,8-quinolinedione derivatives have also been reported fungicide in German Patent Publication No. 4, 208, 874 (1993), but no antifungal activity against human pathogenic fungi was not tested or mentioned.

SUMMARY OF THE INVENTION

The present invention has been completed by synthesizing 6,7-disubstituted-5,8-quinolinedion derivatives and confirming the antifungal activity thereof.

Therefore, an object of the present invention is to provide 6,7-disubstituted-5,8-quinolinedion derivatives expressed in the formula 1, including its preparing method and use as an antifungal agent.

DETAILED DESCRIPTION OF THE PREFERRED EMBODIMENT

The present invention relates to 6,7-disubstituted-5,8-quinolinedion derivatives expressed in the formula 1, (1)

wherein $R_1$ represents phenylamino group substituted 1 to 3 with a substituent selected from the group consisting of a halogen atom and aceto group or $C_1$–$C_{20}$ alkylmercapto group; and $R_2$ represents thiocyano group or $C_1$–$C_{20}$ alkylmercapto group.

The present invention is described in more detail as set forth hereunder.

Among 6,7-disubstituted-5,8-quinolinedion derivatives expressed in the formula 1, preferable compounds are the following formulas 1a, 1b, 1c and 1d,

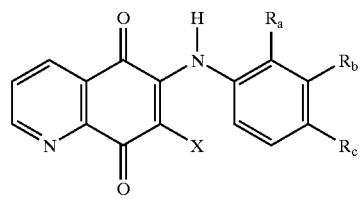
(1a)

wherein $R_a$, $R_b$ and $R_c$ are same or different and a hydrogen atom, a halogen atom or aceto group; and X is a halogen atom;

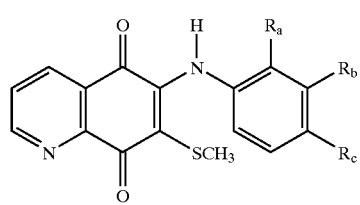
(1b)

wherein $R_a$, $R_b$ and $R_c$ are the same as defined for the compound 1a;

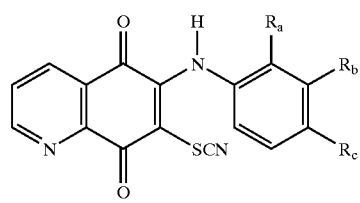
(1c)

wherein $R_a$, $R_b$ and $R_c$ are the same as defined for the compound 1a; and

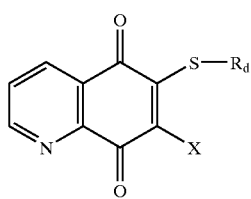

(1d)

wherein $R_d$ is $C_1$–$C_{20}$ alkyl group; and X is a halogen atom.

The examples of 6,7-disubstituted-5,8-quinolindion derivatives of formula 1 are as follows;

6-[(N-4-chlorophenyl)amino]-7-bromo-5,8-quinolindion (compound 1),

6-[(N-3,5-dichlorophenyl)amino]-7-chloro-5,8-quinolindion (compound 2),

6-[(N-4-bromophenyl)amino]-7-bromo-5,8-quinolindion (compound 3),

6-[(N-4-acetophenyl)amino]-7-chloro-5,8-quinolindion (compound 4),

6-[(N-2,3,4-trifulorophenyl)amino]-7-methylmercapto-5,8-quinolindion (compound 5), 6-[(N-4-chlorophenyl)amino]-7-methylmercapto-5,8-quinolindion (compound 6), 6-[(N-4-iodophenyl)amino]-7-methylmercapto-5,8-quinolindion (compound 7), 6-[(N-4-iodophenyl)amino]-7-thiocyano-5,8-quinolindion (compound 8), 6-[(N-4-bromophenyl)amino]-7-thiocyano-5,8-quinolindion (compound 9), 6-[(N-4-chlorophenyl)amino]-7-thiocyano-5,8-quinolindion (compound 10), 6-[(N-4-acetophenyl)amino]-7-thiocyano-5,8-quinolindion (compound 11), 6-[(N-3,5-difulorophenyl)amino]-7-thiocyano-5,8-quinolindion (compound 12), 6-n-ethylmercapto-7-chloro-5,8-quinolindion (compound 13), 6-n-propylmercapto-7-chloro-5,8-quinolindion (compound 14), 6-n-butylmercapto-7-chloro-5,8-quinolindion (compound 15), 6-n-pentylmercapto-7-chloro-5,8-quinolindion (compound 16), 6-n-hecxylmercapto-7-chloro-5,8-quinolindion (compound 17), 6-n-heptylmercapto-7-chloro-5,8-quinolindion (compound 18), 6-n-octylmercapto-7-chloro-5,8-quinolindion (compound 19), 6-n-nonylmercapto-7-chloro-5,8-quinolindion (compound 20).

A method of preparing 6,7-disubstituted-5,8-quinolindion derivatives of formula 1 is shown in the following scheme 1,

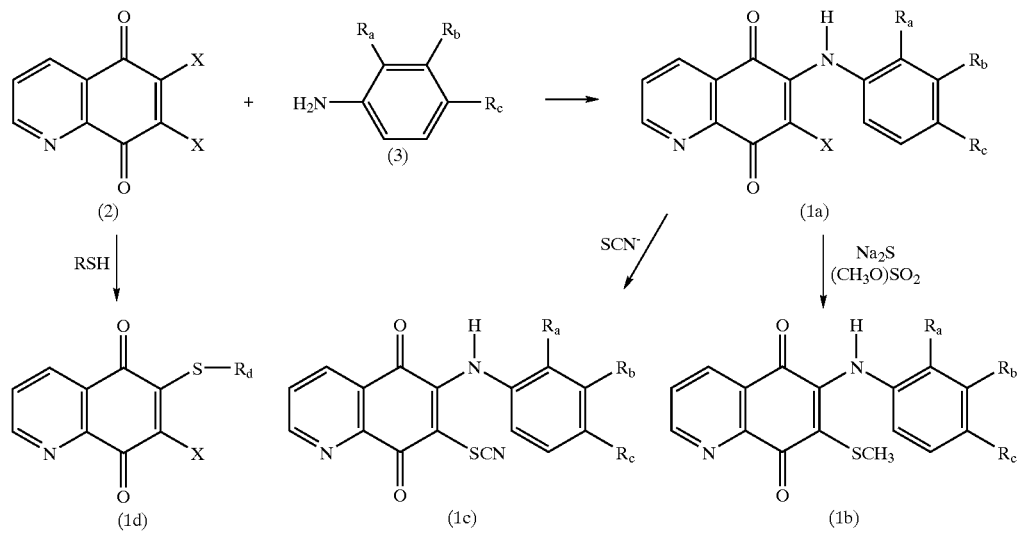

Scheme 1 wherein $R_a$, $R_b$, $R_c$, $R_d$ and X are the same as defined above.

A method of preparing 6,7-dihalo-5,8-quinolindione as starting material expressed in the following formula 2 in the present invention has been disclosed in *J. am. Chem. Soc.*, 82, 1155 (1960) and *Ann. der Chem.*, 624, 108–119 (1959). It is prepared from 8-hydroxyquinoline through 5-nitroso-8-hydroxyquinoline and 5-amino-8-hydroxyquinoline chloride as intermediates.

The detailed preparing method in scheme 1 is described hereunder.

The compound of formula 1a is prepared by condensation reaction of 6,7-dihalo-5,8-quinolindione of formula 2 and an arylamine of formula 3. A solvent used in this reaction is $C_1$–$C_3$ lower alcohol such as methanol, ethanol and isopropanol, acetic acid, dimethylsulfoxide(DMSO) or dioxane, preferably ethanol. The reaction is carried at the temperature of from room temperature to 100° C. for 2–6 hours, preferably at reflux temperature for 3–5 hours.

The compound of formula 1b is prepared by reacting compound 1a dissolved in an alcohol solvent with sodium sulfite($Na_2S$) at room temperature for 2–5 hours, preferably 2–3 hours.

The compound of formula 1c is prepared by reacting compound 1a with ammonium thiocyanate($NH_4SCN$) in acetone. Acetone as a solvent can be replaced to an alcohol such as methanol and ethanol, preferably ethanol.

The compound of formula 1d is prepared by reacting 6,7-dihalo-5,8'-quinolindione of formula 2 with alkylmercaptane($R_d$-SH) at the same reaction condition of the preparing method of compound 1a.

These compounds of formulas 1a, 1b, 1c and 1d are isolated and purified by conventional procedures such as recrystallization and chromatography.

The following examples are intended to be illustrative of the present invention and should not be construed as limiting the scope of this invention defined by the appended claims.

EXAMPLE 1

5-nitroso-8-hydroxyquinoline hydrochloride

To a mixture of 8-hydroxyquinoline (58 g, 0.4 mol) in distilled water, concentrated hydrochloric acid (75 ml) and ice (200 g) was added $NaNO_2$ (30 g) in water (100 ml) at 0–4° C. during 1 hr. The reaction mixture was kept at 0° C. overnight and then filtered by washing with cold water to give 5-nitroso-8-hydroxyquinoline hydrochloide (95%).

EXAMPLE 2

5amino-8-hydroxyquinoline dihydrochloride 5-nitroso-8-hydroxyquinoline chloride (40 g) was added to a mixture of water (160 ml) and 5N-NaOH (260 ml) and heated to 40° C. $Na_2S_2O_4$ (95 g) was added to the reaction mixture wraith increasing temperature to 75–80° C. The reaction mixture was cooled to 50° C. and 12N-HCl (250 ml) was added to it. Then the reaction mixture was cooled to 0° C. and filtered to give 5-amino-8-hydroxyquinoline dihydrochloride (34 g, 69%).

EXAMPLE 3

6,7-dichloro-5,8-quinolindion of Formula 2

After addition of 5-amino-8-hydroxyquinoline dihydrochloride (9 g) to hydrochloric acid (81 g), the reaction mixture was heated to 60° C. and $NaClO_3$ (4.5 g) was added. The reaction mixture was stirred for 30 min at 50–60° C., filtered and recrystallized twice with buthanol to give yellow precipitate of 6,7-dichloro-5,8-quinolindion (90%).

m. p.: 221–222° C.

EXAMPLE 4

6,7-dibromo5,8-quinolindion of Formula 2

After addition of 5-amino-8-hydroxyquinoline dihydrochloride (9 g) to hydrobromic acid (81 g), the reaction mixture was heated to 60° C. and $NaBrO_3$ (7.5 g) was added. The reaction mixture was stirred for 30 min at 50–60° C., filtered and recrystallized twice with buthanol to give yellow precipitate of 6,7-dibromo-5,8-quinolindion (67%).

m. p.: 243–245° C.

EXAMPLE 5

6-[(N-4-chlorophenyl)amino]-7-bromo-5,8-quinolindione of Formula 1

$CeCl_3$ (0.1 mmol) as a catalyst and 4 equivalents of 4-chloroaniline (10 mmol) were added to 6,7-dibromo-5,8-quinolindion (10 mmol) dissolved in ethanol (100 ml). The reaction mixture was heated at reflux for 8 hrs. After reading the completion of reaction by TLC, it was cooled, filtered, and recrystallized with ethanol to give redish powder of 6-[(N-4-chlorophenyl)amino]-7-bromo-5,8-quinolidione.

EXAMPLE 6

6-[(N-4-chlorophenyl)amino]-7-methylmercapto-5,8-quinolidione of Formula 6

Dimethylsulfate (12 mmol) was added to 6-[(N-4-chlorophenyl)amino]-7-bromo-5,8-quinolidione (10 mmol) dissolved in ethanol (100 ml). The reaction mixture was stirred for 2 hrs at room temperature. The reaction mixture was cooled, filtered, and recrystallized with ethanol to give 6-[(N-4-chlorophenyl)amino]-7-methylmercapto-5,8-quinolidione.

EXAMPLE 7

6-[(N-4-chlorophenyl)amino]-7-thiocyano-5,8-quinolidione of Formula 10

1 equivalent of ammonium thiocyanate($NH_4SCN$) was added to 6-[(N-4-chlorophenyl)amino]-7-bromo-5,8-quinolidione (1 g). The reaction mixture was heated at reflux for 3 hrs. After reading the completion of reaction by TLC, it was cooled, filtered, and recrystallized with ethanol to give 6-[(N-4-chlorophenyl)amino]-7-thiocyano-5,8-quinolidione.

EXAMPLE 8

6-ethylcercapto-7-chloro-5,8-quinolindione of Formula 13

$CeCl_3$ (0.1 mmol) as a catalyst and 1 equivalent of sodium sulfide($Na_2S$) were added to 6,7-dichloro-5,8-quinolindion (1 g) dissolved in ethanol (100 ml). The reaction mixture was stirred for 30 min at room temperature. 1 equivalent of ethyl mercaptane was added to the reaction mixture and heated at reflux for 1 hr. The reaction mixture was cooled and filtered to give 6-ethylmercapto-7-chloro-5,8-quinolidione.

Physical properties of the compounds of formula 1 prepared by the above procedure are summarized in table 1a and table 1b.

TABLE 1a

| Comp. No. | State | mp (° C.) | MS (m/e) | IR (KBr, cm$^{-1}$) | $^1$H-NMR (DMSO-d$_6$), ppm |
|---|---|---|---|---|---|
| 1 | Redish Powder | 223~225 | 215, 255, 282, 362(M$^+$) | 3500(s, NH), 3200, 1660 (s, C=O), 1550, 1470 | 7.2~7.4(4H, m, aromatic ring), 8.4~8.9(3H, m, C$_5$H$_3$N), 9.3(1H, s, NH) |
| 2 | Redish Powder | 228~230 | 251, 279, 294, 352(M$^+$) | 3340(s, NH), 3040, 1675(s, C=O), 1600, 1575, 1575, 1380, | 9.21(1H, NH), 7.0~8.4 (8H, m, 2 aromatic ring). |
| 3 | Dark brown Powder | 235~238 | 218, 246, 274, 406(M$^+$) | 3500(s, NH), 1620(s, C=O), 1550, 1470 | 7.1~7.5(4H, m, aromatic ring), 7.8~9.0(3H, m, C$_5$H$_3$N), 9.3(1H, s, NH) |
| 4 | Redish brown Powder | 239~241 | 130, 224, 311, 326(M$^+$) | 3200(s, NH), 3025, 1650 (s, C=O), 1560, 1290, 1255 | 2.55(3H, s, COCH$_3$), 6.57, 7.614(4H, dd, 2 aromatic ring), 8.0~9.23(3H, m, C$_5$H$_3$N), 9.3(1H, s, NH) |
| 5 | Dark redish plate Crystal | 396~400 | 78, 130, 228 260, 316, 338, 350(M$^+$) | 3200(NH), 1670(C=O), 1400, 1250, 1030, 850, 700 | 2.18~2.32(3H, s, SCH$_3$), 6.97~7.41(4H, m, aromatic ring), 8.39~8.50(3H, m, C$_5$H$_3$N), 9.4(1H, m, NH) |
| 6 | Black Powder | 288~290 | 111, 192, 220, 283, 318, 330(M$^+$) | 3200(NH), 1650(C=O), 1550, 1450, 1300, 1200, 1000, 830 | 2.2(3H, s, SCH$_3$), 7.15~7.3(4H, m, aromatic ring), 7.86~9.1(3H, m, C$_5$H$_3$N), 9.39(1H, m, NH) |
| 7 | Redish plate Crystal | 244~246 | 76, 128, 164, 192, 220, 248, 410, 422(M$^+$) | 3200(NH), 1700(C=O), 1550, 1510, 1430, 1300, 1000, 830 | 2.14~2.33(3H, s, SCH$_3$), 6.99~7.07(4H, m, aromatic ring), 7.68~7.92(3H, m, C$_5$H$_3$N), 9.30(1H, m, NH) |
| 8 | Black Powder | 254~257 | 76, 164, 192, 220, 248, 375, 410, 433(M$^+$) | 3200(NH), 2320(C≡N), 1700(C=O), 1400, 1200, 1000, 850, 800 | 7.03~7.87(4H, m, aromatic ring), 8.47~9.07(3H, m, C$_5$H$_3$N), 9.50(1H, s, NH) |
| 9 | Dark brown Powder | 245~248 | 127, 192, 220, 248, 283, 327, 364, 386(M$^+$) | 3200(NH), 2300(C≡N), 1660(C=O), 1500, 1400, 1310, 1200, 800, 700 | 7.18~7.22 (3H, m, aromatic ring), 8.46~8.50(3H, m, C$_5$H$_3$N), 9.45(1H, s, NH) |
| 10 | Black Powder | 279~281 | 75, 111, 164, 192, 220, 283, 318, 341(M$^+$) | 3200(NH), 2320(C≡N), 1700(C=O), 1500, 1400, 1200, 1000, 800, 700 | 7.22~7.48(3H, m, aromatic ring), 7.92~8.50(3H, m, C$_5$H$_3$N), 9.47(1H, s, NH) |

TABLE 1b

| Comp. No. | State | mp (° C.) | MS (m/e) | IR (KBr, cm$^{-1}$) | $^1$H-NMR (DMSO-d$_6$), ppm |
|---|---|---|---|---|---|
| 11 | Brown Powder | 253~257 | 215, 291, 306, 349(M$^+$) | 3300(NH), 2000(C≡N), 1500(C=O), 1200, 1160, 1000 | 2.28~2.32(3H, q, p-COCH$_3$), 7.47~7.75(4H, m, aromatic ring), 8.54~8.85(3H, m, C$_5$H$_3$N), 9.54(1H, s, NH) |
| 12 | Redish Powder | 211~213 | 63, 77, 125, 202, 257, 285, 343(M$^+$) | 3200(NH), 2300(C≡N), 1700(C=O), 1600, 1400, 1310, 1220, 900, 850, 700 | 7.30~7.86(3H, m, aromatic ring), 8.45~8.48(3H, m, C$_5$H$_3$N), 9.31(1H, s, NH) |
| 13 | Dark brown plate Crystal | 328~330 | 91, 263, 298 (M$^+$) | 1700(C=O), 1450(CH$_2$), 1300(CH$_3$), 1200, 1150, 800 | 1.15~1.29(3H, m, 3CH$_3$), 2.63~2.97(2H, t, CH$_2$), 7.96~8.69(3H, m, C$_5$H$_3$N) |
| 14 | Dark brown plate Crystal | 299~302 | 91, 263, 298 (M$^+$) | 1650(C=O), 1450(CH$_2$), 1300(CH$_3$), 1250, 1150, 800 | 1.02~1.12(3H, q, CH$_3$), 3.42~3.72(4H, m, 2CH$_2$), 8.44~9.23(3H, m, C$_5$H$_3$N) |
| 15 | Black plate Crystal | 400° C. Up to | 91, 263, 298 (M$^+$) | 1680(C=O), 1460(CH$_2$), 1310(CH$_3$), 1150, 1050, 800 | 1.06~1.35(3H, q, 3CH$_3$), 2.59~2.60(6H, m, 3CH$_2$), 8.44~9.13(3H, m, C$_5$H$_3$N) |
| 16 | Black plate Crystal | 311~314 | 91, 263, 298 (M$^+$) | 1670(C=O), 1450(CH$_2$), 1300(CH$_3$), 1250, 1000, 800 | 0.94~0.97(3H, q, CH$_3$), 1.15~1.80(8H, m, 4CH$_2$), 8.44~8.58(3H, m, C$_5$H$_3$N) |
| 17 | Dark redish Powder | 289~303 | 91, 263, 298 (M$^+$) | 1670(C=O), 1150(CH$_2$), 1320(CH$_3$), 1130, 820 | 0.93~0.96(3H, q, CH$_3$), 2.01~2.59(10H, m, 5CH$_2$), 7.82~9.09(3H, m, C$_5$H$_3$N) |
| 18 | Dark brown plate Crystal | 128~131 | 55, 134, 190, 225, 288, 323 (M$^+$) | 1650(C=O), 1500(CH$_2$), 1280(CH$_3$), 1140, 890, 830 | 0.88~0.91(3H, q, CH$_3$), 1.33~1.65(12H, m, CH$_2$), 7.89~9.09(3H, m, C$_5$H$_3$N) |
| 19 | Black plate Crystal | 400° C. Up to | 91, 263, 298 (M$^+$) | 1670(C=O), 1530(CH$_2$), 1300(CH$_3$), 1160, 780 | 0.87~1.28(3H, m, CH$_3$), 2.58~2.63(14H, m, 7CH$_2$), 7.74~9.04(3H, m, C$_5$H$_3$N) |
| 20 | Yellow | 142~145 | 55, 69, 134, | 1680(C=O), 1460(CH$_2$), | 0.87~0.92(3H, q, CH$_3$), |

TABLE 1b-continued

| Comp. No. | State | mp (° C.) | MS (m/e) | IR (KBr, cm$^{-1}$) | $^1$H-NMR (DMSO-d$_6$), ppm |
|---|---|---|---|---|---|
| | Powder | | 190, 225, 320, 351(M$^+$) | 1280(CH$_3$), 1200, 1110, 890 | 1.30~2.59(10H, m, 8CH$_2$), 7.94~9.05(3H, m, C$_5$H$_3$N) |

The compounds of 6,7-disubstituted-5,8-quinolindione derivatives of formula 1 and its pharmaceutically acceptable salts have excellent antifungal activity. A pharmaceutical composition containing the compounds as an effective ingredient is disclosed in the present invention. Said pharmaceutically acceptable salts include hydrochloric acid salt, sulfuric acid salt and bisulfite salt.

A pharmaceutical composition comprises a compound of formula 1, pharmaceutically acceptable carriers, fillers, and other additives. The carrier(s) must be 'acceptable' in the sense of being compatible with other ingredients of the formulation and not deleterious to the recipient thereof.

The compositions of the invention include those in a foam especially formulated for a)oral administration such as tablets, capsules, troches, solutions, emulsions and suspensions, b)parenteral administration by injection presented in such forms as suspension, solutions, emulsions and powder for constitution with a suitable vehicle, e.g. sterile water, before use, and c)topical administration in the form of ointments, creams, gels, or lotions. Pharmaceutically acceptable carriers in use for suitable formulations are: binding agents, lubricants, diluents, solubilizers, disintegrants, stabilizers, emulsifing agents, colorants and aromatics for oral administration; preservatives, solubilizers, and stabilizers for parenteral administration; and bases, diluents, lubricants, thickeners, and preservatives for topical administration. These pharmaceutically acceptable formulations are administered orally, parenterally by intravenous, subcutaneous and intraperitoneal injection/infusion, or topically. In oral administration, antacids can be combined in a pharmaceutical composition to prevent from degradation by gastric acid and tablets may be coated to give enteric-coated tablet.

The dose varies depending on age, body weight, sex, symptom and the like of patients, and types of administration but it is usually 0.01–200 mg/kg/day, which is administered in several doses a day, preferably in a single dose or several doses.

Examples for formulation comprising 6,7-disubstituted-5,8-quinolindion derivatives of formula 1 and its pharmaceutically acceptable salts as an effective ingredient are described but it should be noted that the present invention is not limited to these exemplifications.

FORMULATION EXAMPLE 1

Capsule for Oral Administration 100 mg of an effective compound, 10 mg of anhydrous silicic acid, 190 mg of microcrystalline cellulose, 5 mg of magnesium stearate, 60 mg of starch and sodium gluconate and 135 mg of anhydrous calcium hydrogenphosphate were mixed and stirred. The mixture was put into hard gelatin capsules to give a capsule drug.

FORMULATION 2

Injection for Parental Administration 100 mg of an effective compound, 180 mg of mannitol, 26 mg of sodium hydrogenphosphate were dissolved in 2,974 mg of sterile water to give an injection solution.

FORMULATION 3

Ointment for Topical Administration 2 g of an effective compound, 7 g of lanoline tablets and effective amount of white ointment to give 10 g of total weight.

Antifungal activities of the compounds of formula 1 according to the present invention are determined by the following Experimental Examples.

EXPERIMENTAL EXAMPLE 1

Determination of Minimum Inhibitory Concentration(MIC) Values

The minimum inhibitory concentration (MIC), which indicates the lowest concentration of the active ingredient in the growth medium, was determined by solid medium dilution method. Pathogens strains used are *Candida albicans* ATCC10231, *Candida glabrata* ATCC2001, *Candida tropicalis* ATCC8775, *Candida parasilosis* ATCC22019, *Cryptococuss neoformans* KCTC7223.

4 mg of a test compound was dissolved in 2 ml of dimethylfulfoxide(DMSO) to produce solutions having a concentration of 2 mg/ml for use and serial two-fold dilution was prepared. The test medium was Sabouraud's agar. 50 μl aliquot of serial two-fold dilution was added to 1 ml of agar medium in 10×1.2 cm petri dishes to be 100, 50, 25, 12.5 6.3, 1.6, and 0.8 μg/ml of test compound concentration and the slant was prepared by tilting the petri dishes. The MIC value without containing a test compound was determined in order to test an effect of a solvent to an antifungal activity. Hyphae with a diameter of 2 mm were inoculated with 2×10$^5$ CFU. After the medium was cultured for 3 days at 30° C., the MIC values were determined. Control drugs were fluconazole and ketoconazole. The datas are shown in table 2.

TABLE 2

| | MIC (μg/ml) | | | | |
|---|---|---|---|---|---|
| Compound No. | C. albicans | C. glabrata | C. tropicallis | C. parapsilosis | C. neoformans |
| Compound No. 1 | 6.3 | 12.5 | 12.5 | 25.0 | 12.5 |
| Compound No. 2 | 12.5 | 12.5 | 25.0 | 6.3 | 12.5 |
| Compound No. 3 | 6.3 | 6.3 | 12.5 | 25.0 | 6.3 |
| Compound No. 4 | 1.6 | 3.2 | 3.2 | 6.3 | 12.5 |
| Compound No. 5 | 1.6 | 3.2 | 3.2 | 25.0 | 6.3 |
| Compound No. 6 | 12.5 | 6.3 | <0.8 | 25.0 | 12.5 |
| Compound No. 7 | 6.3 | 3.2 | 3.2 | 25.0 | 3.2 |

TABLE 2-continued

| | MIC (μg/ml) | | | | |
|---|---|---|---|---|---|
| Compound No. | C. albicans | C. glabrata | C. tropicallis | C. parapsilosis | C. neo-formans |
| Compound No. 8 | 12.5 | 12.5 | 12.5 | 100.0 | 12.5 |
| Compound No. 9 | <0.8 | 6.3 | <0.8 | <0.8 | 3.2 |
| Compound No. 10 | 12.5 | 12.5 | 12.5 | 100.0 | 6.3 |
| Compound No. 11 | 6.3 | 25 | 3.2 | 3.2 | <0.8 |
| Compound No. 12 | 12.5 | 12.5 | 3.2 | 1.6 | <0.8 |
| Compound No. 13 | 12.5 | 50 | 100 | 3.2 | 6.3 |
| Compound No. 14 | 12.5 | 50 | 50 | 12.5 | 3.2 |
| Compound No. 15 | 25 | 12.5 | 100 | 25 | 12.5 |
| Compound No. 16 | 3.2 | 12.5 | 50 | 6.3 | 25 |
| Compound No. 17 | 25 | 50 | 50 | 25 | 12.5 |
| Compound No. 18 | 6.3 | 50 | 12.5 | 6.3 | 12.5 |
| Compound No. 19 | 12.5 | 25 | 12.5 | 3.2 | 12.5 |
| Compound No. 20 | 50 | 50 | 6.3 | 25 | 25 |
| Fluconazole | 25.0 | 25.0 | 100.0 | 12.5 | 25.0 |
| Ketoconazole | 12.5 | 12.5 | 12.5 | 12.5 | 12.5 |

As shown in table 2, the compounds of the present invention show excellent inhibitory activity against *Candida albicans, C. glabrata, C. tropicalis, C. parapsilosis, Cryptococuss neoformans* and the like and their activities are superior or similar to those of the control drugs, fluconazole and ketoconazole. Especially, the growth of fungus was completely inhibited against 5 types of strains when the concentration of the compound was 50 μg/ml.

EXPERIMENTAL EXAMPLE 2

*C. albicans* ($1\times10^7$) isolated was inoculated to Sabouraud's agar, suspended in a physiological saline solution, and injected into tail vein of a rat. Strains to kill a rat within 48 hours were selected. *C. albicans* ($2\times10^6$ which is concentration to kill a rat within 48 hours) suspended in a physiological saline solution was injected and infected into tail veins of 125 rats. Each concentration (10, 2, 0.5, 0.1, 0.025 mg/kg) of the compounds of table 3 was administered to each 10 rats. After infecting with Candida strain, each compound was administered to each 10 rats. Fluconazol as a control drug was also administered with 10, 2, 0.5 and 0.1 mg/kg of concentrations. A physiological saline solution containing 0.2% tween 20 was administered as a control group. The datas are shown in table 3.

TABLE 3

| Compound No. | $ED_{50}$ ± SD (n = 5), (mg/kg) |
|---|---|
| Compound No. 1 | 0.06 ± 0.03 |
| Compound No. 2 | 0.07 ± 0.03 |
| Compound No. 3 | 0.06 ± 0.03 |
| Compound No. 4 | 0.40 ± 0.25 |
| Fluconazole | 6.00 ± 1.70 |

According to the table 3, while $ED_{50}$ of a control drug, fluconazole, was 6.00 mg/kg of the concentration to a rat infected with *C. albicans*, each $ED_{50}$ of the compounds 1, 2, 3, and 4 was 0.06, 0.07, 0.06 and 0.04 mg/kg of the concentration.

EXPERIMENTAL EXAMPLE

Survival Prolongation Effect of a Rat Infected with *C. albicans*

Figure 2:
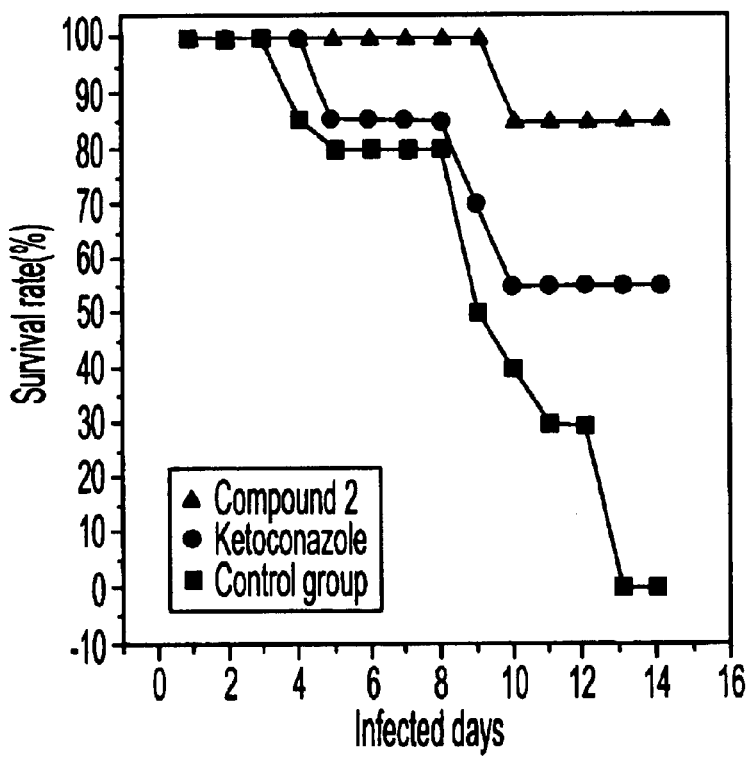
Figure 3:
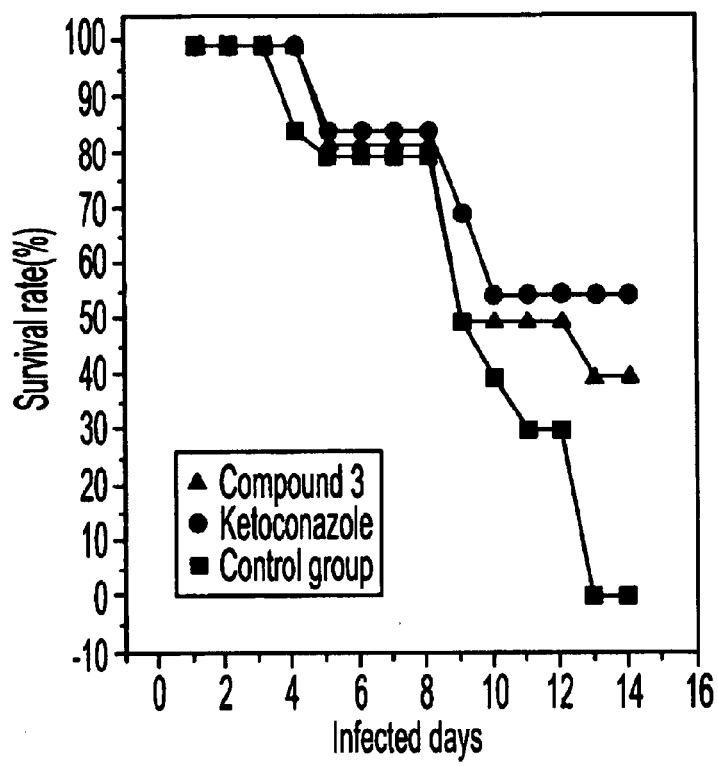
Figure 4:
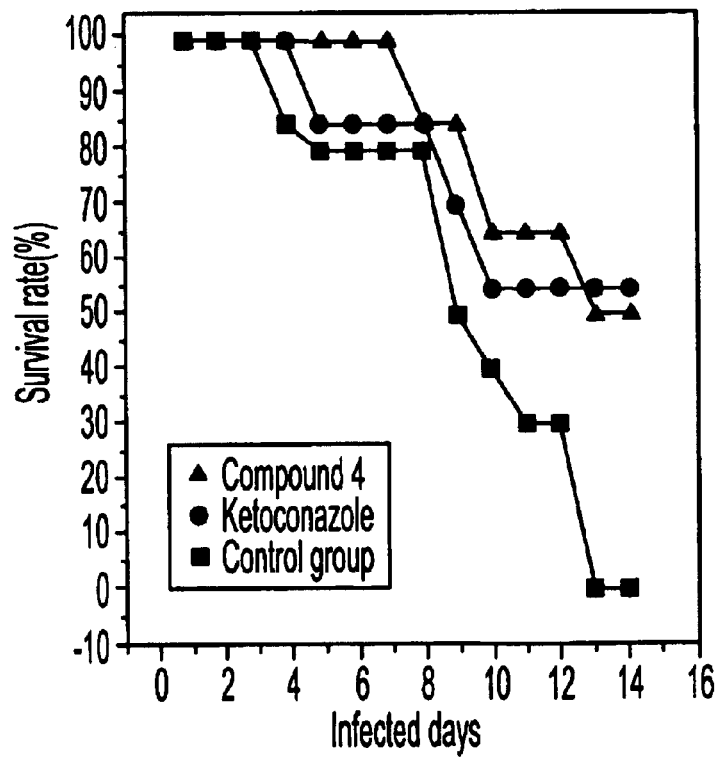

$2\times10^4$/0.1 ml of *C. albicans* suspended in physiological saline was injected into 49 rats via tail vein to infect and divided to 4 groups of 7 rats. The concentration of effective dose ($ED_{50}$) was injected intraperitoneally once daily for 14 days after 4 days of infection. In other words, 0.06, 0.07, 0.06 and 0.04 mg/kg of the test compounds 1, 2, 3, and 4 and 6.00 mg/kg of the control drug, ketoconazole were injected to determine the survival rate. The results were shown in FIGS. 1 through 4.

According to FIGS. 1 through 4, the compounds of the present intention show similar inhibitory activity at lower concentration than that of ketoconazole which is the control drug. Therefore, 6,7-disubstituted-5,8-quinolindione derivatives of formula 1 have excellent inhibitory activity against various fungus.

Based on foregoing, the compounds of formula 1 of the present invention are useful for the treatment of a variety of fungal infections in human and animals.

What is claimed is:

1. A compound of the formula

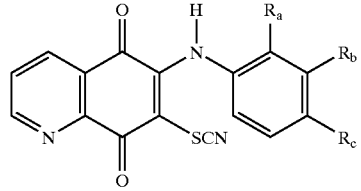

wherein $R_a$, $R_b$ and $R_c$ are same or different, and are selected from the group consisting of a hydrogen atom, a halogen atom and an aceto group.

2. The compound according to claim 1, wherein the compound is selected from the group consisting of:

6-[(N-4-iodophenyl)amino]-7-thiocyano-5,8-quinolinedione,

6-[(N-4-bromophenyl)amino]-7-thiocyano-5,8-quinolinedione,

6-[(N-4-chlorophenyl)amino]-7-thiocyano-5,8-quinolinedione,

6-[(N-4-acetophenyl)amino]-7-thiocyano-5,8-quinolinedione, and

6-[(N-3,5-difulorophenyl)amino]-7-thiocyano-5,8-quinolinedione.

3. A process for preparing a compound of formula 1a

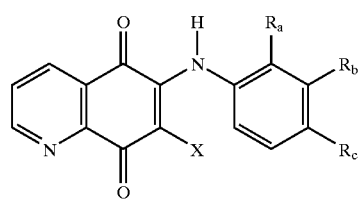

(1a)

by reacting a 6,7-dihalo-5,8-quinolinedione of formula 2 and an arylamine of formula 3,

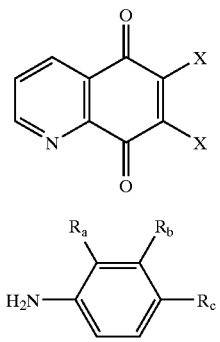

wherein:

$R_a$, $R_b$ and $R_c$ are same or different, and are selected from the group consisting of a hydrogen atom, a halogen atom and an aceto group;

X is a halogen atom, and each instance of X is the same or different; and ethanol is used as a solvent.

4. The process for preparing the compound of formula 1a according to claim 3, wherein said reaction is performed at a temperature between room temperature and 100° C.

5. The process for preparing the compound of formula 1a according to claim 3, wherein said reaction is preformed for 2 to 6 hours.

6. A process for preparing the compound of formula 1c

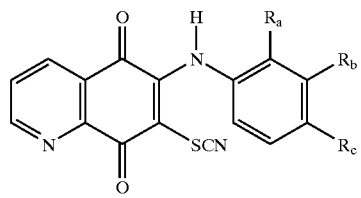

by reacting the compound of formula 1a

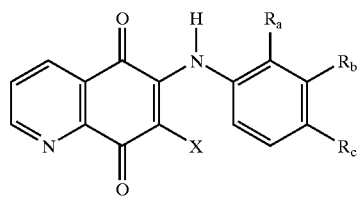

with ammonium thiocyanate($NH_4SCN$), wherein $R_a$, $R_b$ and $R_c$ are same or different, and are selected from the group consisting of a hydrogen atom, a halogen atom and an aceto group; and X is a halogen atom.

7. The process for preparing the compound of formula 1c according to claim 6, wherein said reaction is performed in acetone by heating at reflux.

8. A unit dosage form comprising an amount of a compound of claim 1 and a pharmaceutically acceptable excipient or a carrier.

9. A method for treating a fungus-related disease in a mammal, which comprises administering to a mammal in need thereof an effective amount of a compound of claim 1.

10. The method of claim 9, wherein the mammal is human.

* * * * *